US006528490B2

(12) United States Patent
Steck et al.

(10) Patent No.: US 6,528,490 B2
(45) Date of Patent: *Mar. 4, 2003

(54) OENOTHEIN MEDICAMENTS

(75) Inventors: Warren Steck, Saskatoon (CA); Mark Hetherington, Saskatoon (CA)

(73) Assignee: Fytoken Products, Inc., Saskatchewan (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/433,977

(22) Filed: Nov. 4, 1999

(65) Prior Publication Data

US 2003/0004131 A1 Jan. 2, 2003

(30) Foreign Application Priority Data

Sep. 10, 1999 (CA) ............................................. 2282185

(51) Int. Cl.[7] ............................................. A61K 35/78
(52) U.S. Cl. ........................ 514/25; 514/38; 514/738; 514/185; 536/4.1; 424/59; 424/195.1
(58) Field of Search ........................ 514/25, 38, 738, 514/185; 536/4.1; 424/59, 195.1

(56) References Cited

U.S. PATENT DOCUMENTS

| | | | |
|---|---|---|---|
| 5,073,545 A | | 12/1991 | Arima et al. |
| 5,198,217 A | | 3/1993 | Vedros |
| 5,466,452 A | | 11/1995 | Whittle |
| 5,525,594 A | * | 6/1996 | Gourest et al. ............... 514/25 |
| 5,804,168 A | | 9/1998 | Murad |
| 5,843,911 A | | 12/1998 | Nakahara et al. |
| 5,843,987 A | | 12/1998 | Rajagopalan et al. |
| 5,879,711 A | | 3/1999 | Sequeira et al. |

FOREIGN PATENT DOCUMENTS

| | | | | |
|---|---|---|---|---|
| DE | 3605250 | * | 7/1987 | |
| DE | 36 05 250 C1 | | 7/1987 | .......... A61K/35/78 |
| DE | 39 00 023 A1 | | 7/1990 | .......... C07H/17/07 |
| EP | 234019 | | 9/1987 | |
| FR | 2712495 | * | 5/1995 | |
| FR | 2712594 | | 5/1995 | .......... C07H/13/08 |
| HU | 9603466 | | 11/1998 | |
| JP | 58038209 | | 3/1983 | |

OTHER PUBLICATIONS

Hendry et al. "Iron–induced oxygen radical metabolism in waterlogged plants". HCAPLUS 103:211253, New Phytol. (1985), 101(1), 199–206.*

Juan et al. "Anti–inflammatory effects of a substance extracted from *Epilobium angustifolium*". Medline: 88180554 Agents and Actions, (1988 Feb.) 23 (1–2), 106–107.*

Ducrey et al. "Inhibition of 5–alpha–reductase and aromatase by the ellagitannins oenothein A and oenothein B from Epilobium species." Planta Med. (1977), 63(2), 111–114.*

Dijkstra et al. (1996). "Repertorium 96/97" *SDU Service-centrum Uitgeveverijen*.

(List continued on next page.)

Primary Examiner—Samuel Barts
Assistant Examiner—Devesh Khare
(74) Attorney, Agent, or Firm—Bret E. Fields; Bozicevic, Field & Francis

(57) ABSTRACT

The invention provides medicaments comprising an oenothein, including topical formulations for use as free radical scavengers, or to treat irritation, or to treat inflammation. The oenothein for use in such formulations, such as oenothein-A or oenothein-B, may be purified from natural sources, such as plant material (e.g. *Epilobium angustifolium*).

24 Claims, 6 Drawing Sheets

OTHER PUBLICATIONS

Ducrey et al. (1997). "Inhibition of 5–alpha–reductase and aromatase by the ellagitannins oenothein A and oenothein B from Epilobium species" *Planta Medica*, vol. 63(2): 111–114.

Hiermann (1987). "The investigation of active compounds from Epilobium species. 4$^{th}$ Communication. The anti–inflammatory effect of different Epilobium species and their influence on prostaglandin" *Scientia Pharamaceutica*, vol. 55(2): 111–116.

Kotaro (1997). "Antiallergy action of *Rubus suavissimus*" *Chemical Abstracts*, vol. 127(9): 52–59.

Luepke, N. P. & Kemper, F. H., (1986), The HETCAM Test: An Alternative to the Draize Eye Test, Food and Chemical Toxicology, 24:495–496.

Spielmann et al., (1997), CAM–based Assays, Food and Chemical Toxicology, 35:39–66.

Okuda, T., Yoshida, T. & Hatano, T. (1989), Ellagitannins as Ative Constituents of Medicinal Plants, Planta Med, 55(2):117–22.

Miyamoto, K., et al. (1993), Jpn J Cancer Res, Antitumor Activity of Oenothein B., a Unique Macroyclic Ellagitannin, 84(1):99–103.

Aoki, K. et al. (1995), Biochem Biophys Res Commun, A Macrocircular Ellagitannin, Oenothein B., Suppresses Mouse Mammary Tumor Gene Expression via Inhibition of Poly(ADP–ribose) Glycohydrolase, 210(2): 329–37.

Lesuisse, D. et al. (1996), J Nat Prod, Determination of Oenothein B as the Active 5–Alpha–Reductase–Inhibiting Principle of the Folk Medicine Epilobium Parviflorum, 59(5): 490–2.

Hiermann, et al. (1991), Planta Medica, 57:357.

* cited by examiner

Oenothein-A

Oenothein-B

OENOTHEIN MEDICAMENTS

FIELD OF THE INVENTION

The invention is in the field of compositions and methods for treatment of inflammation, irritation and the effects of free radicals, using oenothein ellagitannins.

BACKGROUND OF THE INVENTION

Ellagitannins are a diverse family of naturally-occurring compounds consisting of a central core of glucose esterified with hexahydroxydiphenic acid. Ellagitannins are known as active constituents of a variety of medicinal plants (Okuda and Hotano, 1989, *Planta Med.* 55(2):117). For example, U.S. Pat. No. 5,843,911 issued Dec. 1, 1998 discloses the use of ellagitannins having galloyl and hexahydroxydiphenoyl substituents as hyaluronidase enzyme inhibitors for topical application, to enhance water retention in skin by preventing the hydrolysis of hyaluronic acid. The ellagitannins disclosed in U.S. Pat. No. 5,843,911 are identified as "GOD-type" ellagitannins, extractable from a variety of plants.

U.S. Pat. No. 5,525,594 issued Jun. 11, 1996 discloses the use of the ellagitannin oenothein-B (which is not a "GOD-type" ellagitannin as defined in U.S. Pat. No. 5,843,911) for the treatment of hyperandrogenic disorders by oral, rectal or parenteral administration (also reported in Lesuisse et al., 1996, *J. Nat. Prod.* 59(5):490). In this treatment, the mechanism of action of oenothein-B is taught to be the inhibition of 5-reductase, an enzyme responsible for the conversion of testosterone to dihydrotestosterone. Both oenothein-A and oenothein-B from Epilobium species have been shown to have similar pharmocologic activity, evidenced by 5-reductase and aromatase inhibition (Ducrey et al., 1996, *Planta Medica* 63:111). It is disclosed in U.S. Pat. No. 5,525,594 that oenothein-B may be extracted from various Onagraceae plants (evening-primrose family), including *Epilobium parviflorum*. Ducrey et al., 1996, supra, disclose the extraction of oenotheins-A and B from *E. capense*, and the quantitation of oenothein-B in a variety of old world Epilobium species, including Old World *E. angustifolium* L (Rosebay Willowherb). The apparent antiviral and antitumour activities of oenothein-B are also discussed by Ducrey et al., 1996, supra, and in U.S. Pat. No. 5,525,594.

Aqueous extracts of Old World *Epilobium angustifolium* have been suggested for use as oral anti-inflammatories (German Patent No. 3,605,250 of Jul. 16, 1987), and the active ingredient in such extracts has been identified as the flavonoid compound myricetin glucuronide (3,3'4',5,5',7-hexahydroxyflavone-3-O-glucuronide; see Hiermann et al., 1991, *Planta Medica* 57:357 and German Patent 3,900,023 of Jul. 12, 1990).

It has previously been disclosed, by the present inventors, that crude aqueous extracts of New World *Epilobium angustifolium* (Canadian Willowherb) have anti-irritant and anti-inflammatory properties when applied to human skin.

Exposure of skin to sunlight can cause inflammation directly as a result of the harmful effects of ultraviolet light. In the presence of atmospheric oxygen, sun-exposed skin may also be indirectly damaged by exposure to free radicals of oxygen generated by solar radiation. There remains a need in the art for compounds that may be used to treat inflammation, irritation and exposure to free radicals.

SUMMARY OF THE INVENTION

It has surprisingly been discovered that oenotheins are potent topical anti-inflammatories, anti-irritants and free radical scavengers (useful for treating exposure to free radicals). These activities provide unexpected advantages in topical formulations or medicaments, for example to ameliorate the effects of sunlight on skin. Accordingly, the invention provides formulations comprising an oenothein, including formulations for topical use as free-radical-scavengers or as a prophylactic against damage caused by sunlight or other ionizing radiation, or to treat irritation and inflammation (including irritation and inflammation caused by exposure to sunlight or other agents). The oenothein for use in such formulations may for example be oenothein-A or oenothein-B. The oenothein may be purified from natural sources, such as plant material, or it may be prepared synthetically.

Other aspects of the invention include methods of formulating topical medications for treatment of inflammation, irritations or exposure to free radicals, comprising adding a known amount of an oenothein to such compositions (prior to the present invention, there was no motivation to determine the amount of oenothein being administered in herbal remedies, such as *Epilobium angustifolium* extracts). In light of the present invention, plant extracts for use in such formulations may now be assayed to determine the concentration of oenothein in the extracts so that dosages may be formulated more reliably. For example, New World *Epilobium angustifolium* extracts may be assayed for oenothein-B content. Packaging for formulations of the invention may include text that indicates that the formulations are useful for prophylaxis of sunlight induced damage, as free radical scavengers for treating exposure to free radicals, or for treating inflammation or irritation, such text may optionally disclose that the formulations contain an oenothein.

In another aspect of the invention, new plant extracts found to contain an oenothein may be used topically to ameliorate the effects of sunlight, as anti-irritants, as anti-inflammatories, or for treating exposure to free radicals. For example, Epilobium spp. other than *Epilobium angustifolium* may be used for making such extracts where they contain oenothein-A or oenothein-B or mixtures thereof.

DETAILED DESCRIPTION OF THE INVENTION

Figure 1:
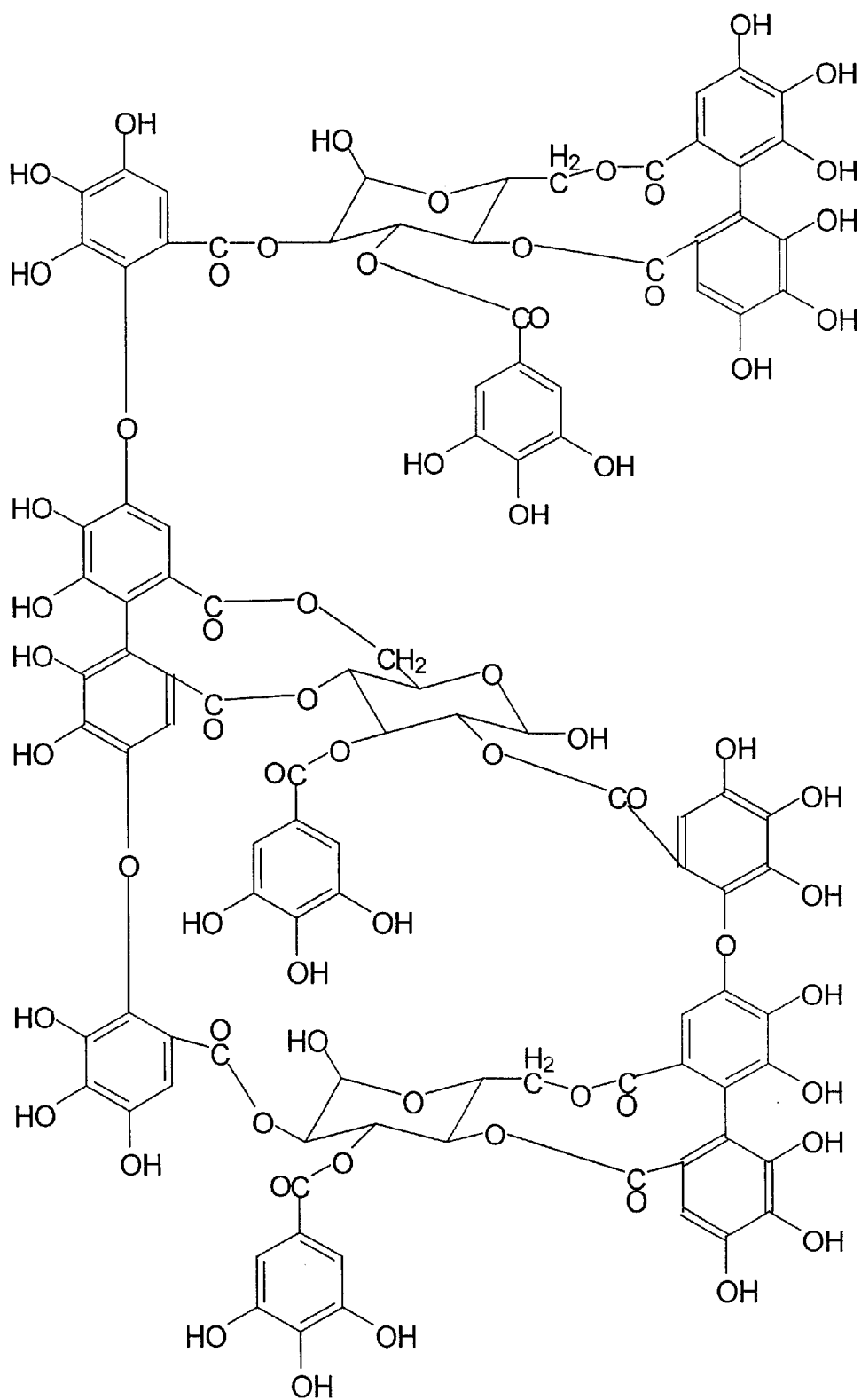
FIG. 1 is a drawing of the known structure of oenothein-A (from Ducrey et al., 1996, supra).
Figure 2:
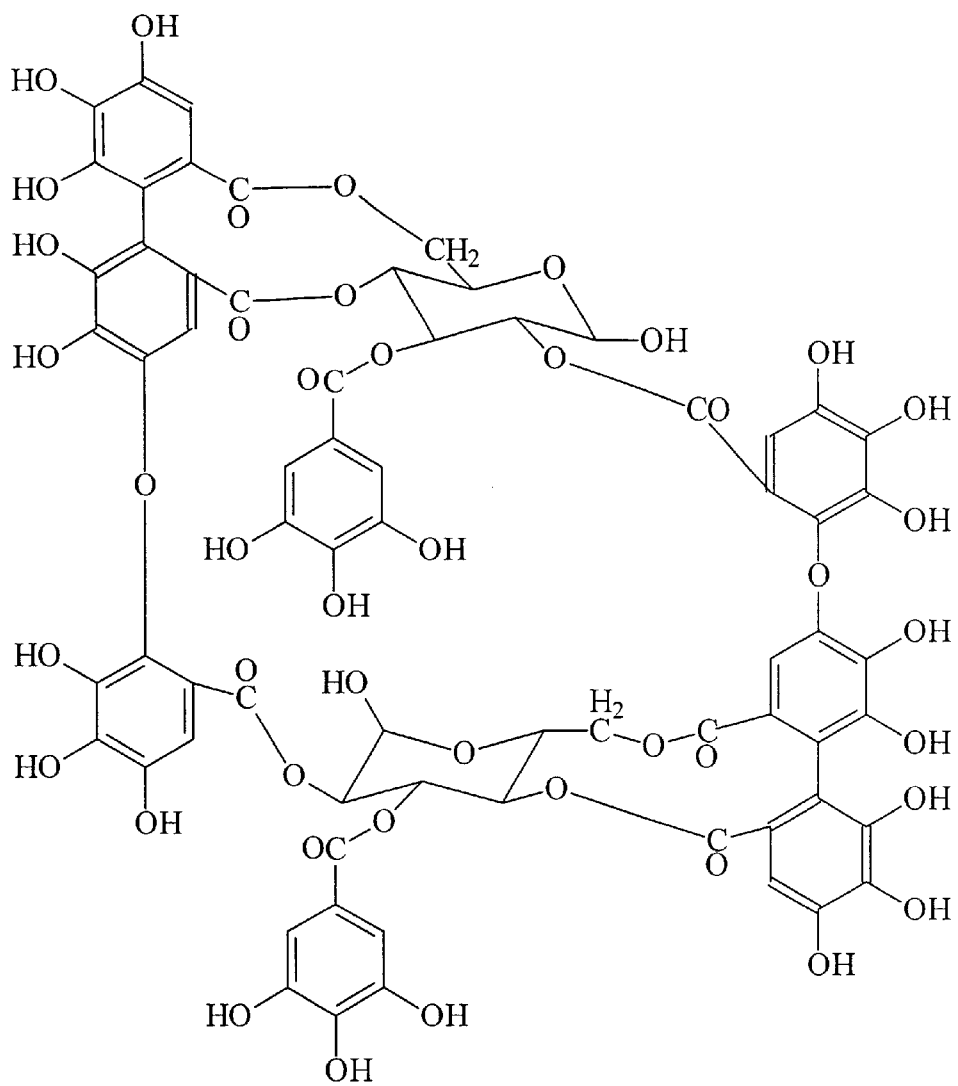
FIG. 2 is a drawing of the known structure of oenothein-B (from Ducrey et al., 1996, supra).

In one aspect, the invention provides formulations or medicaments for treating a variety of symptoms, diseases or disorders, including inflammation and irritation, such as inflammation and irritation of the skin. Inflammation and irritation are characteristic of a wide variety of skin diseases treatable with the compounds of the invention, including psoriasis and eczema. As used herein, the term "irritation" includes conditions medically recognized as pruritus (itching) or prurigo, such as simple or acute pruritis, pruritus ani, pruritus essential, pruritus estivalis, pruritus hiemalis, pruritus senilis, symptomatic pruritus and pruritus vulvae. Anti-irritant formulations of the invention accordingly include anitpruritic formulations. As used herein, the term "inflammation" includes conditions medically recognized as dermatitis, including actinic dermatitis, dermatitis aestivalis, allergic dermatitis, atopic dermatitis, berlock dermatitis, dermatitis calorica, cercarial dermatitis, contact dermatitis, cosmetic dermatitis, exfoliative dermatitis, dermatitis herpetiformis, dermatitis hiemalis, infectiosa eczematoides, dermatitis medicamentosa, dermatitis multiformis, dermatitis capillitii, poison ivy dermatitis, primary dermatitis, radiation dermatitis, rhus dermatitis, dermatitis seborrheica, stasis dermatitis, dermatitis venenata, dermatitis verrucosa and x-ray dermatitis. The irritation or inflammation treatable using compositions of the invention may accordingly include such conditions as caused by a wide variety of agents, including radiation (such as sunlight and ionizing radiation), chemicals, physical insult (traumatic or prolonged), foreign bodies, electricity, thermic causes (heat or cold) or microorganisms.

In some aspects, the invention provides methods of medical or cosmetic treatment, in which a therapeutic or prophylactic dose of an oenothein is administered, such as by administration of a pharmacologically acceptable formulation. Such formulations of the invention may comprise oenothein-B or oenothein-A and a pharmacologically acceptable excipient or carrier, and may comprise a pharmaceutically acceptable salt of the oenothein. In some embodiments, such formulations may comprise a therapeutically or prophylactically effective amount sufficient to alter, and preferably inhibit, inflammation or irritation, or to quench free radicals.

As used herein "pharmaceutically acceptable carrier" or "excipient" includes any and all creams, gels, solvents, dispersion media, coatings, antibacterial and antifungal agents, isotonic and absorption delaying agents, and the like that are physiologically compatible and do not significantly adversely effect the pharmaceutical properties (e.g. toxicity and effectiveness) of the oenothein, such as are conventionally used in the cosmetic and pharmaceutical arts. In one embodiment, the carrier is suitable for topical administration. In some embodiments, topical administration includes administration to the skin or mucosa, including surfaces of the lung and eye. Under some conditions, oenotheins may undergo hydrolysis in acid or base, so that pharmaceutically acceptable carriers or excipients may include pH buffers to maintain an acceptable pH for pharmaceutical activity (see Daniel et al., 1991, *J. Natural Products* 54(4):946, for a discussion of the effects of pH on ellagitannins).

A "therapeutically effective amount" refers to an amount effective, at dosages and for periods of time necessary, to achieve the desired therapeutic result, such as reduction or reversal of inflammation or irritation. A therapeutically effective amount of an oenothein may vary according to factors such as the disease state, age, sex, and weight of the individual, and the ability of the oenothein to elicit a desired response in the individual. Dosage regimens may be adjusted to provide the optimum therapeutic response. A therapeutically effective amount is also one in which any toxic or detrimental effects of the oenothein are outweighed by the therapeutically beneficial effects.

A "prophylactically effective amount" refers to an amount effective, at dosages and for periods of time necessary, to achieve the desired prophylactic result, such as preventing or inhibiting the rate of inflammation or irritation or the onset of inflammation or irritation, or quenching of free radicals. A prophylactically effective amount can be determined as described above for the therapeutically effective amount.

In particular embodiments, a preferred range for therapeutically or prophylactically effective amounts of an oenothein may be 0.1% to 10% by weight. One method of cosmetic, prophylactic or therapeutic treatment is to apply an oenothein topically to the area of inflammation or irritation. Dosage values may vary with the severity of the condition to be alleviated. It is to be further understood that for any particular subject, specific dosage regimens may be adjusted over time according to the individual need and the judgement of the person administering or supervising the administration of the compositions, and that dosage ranges set forth herein are exemplary only and are not intended to limit the scope or practice of the methods of the invention.

In accordance with another aspect of the invention, therapeutic compositions of the present invention, comprising an oenothein, may be provided in containers having labels that provide instructions for use of the formulation to: treat inflammation, treat irritation, scavenge free radicals, or ameliorate the effects of exposure to sunlight. The labels may also disclose that the compositions comprise an oenothein.

It has previously been disclosed, by the present inventors, that crude aqueous extracts of *Epilobium angustifolium* have anti-irritant and anti-inflammatory properties when applied to human skin. In accordance with the present invention, it has been determined that the concentration of oenothein-B in such extracts did not exceed 9.6% by weight. Accordingly, with the unexpected discovery that oenothein-B is an active ingredient in such extracts, the present invention provides for novel topical formulations of *Epilobium angustifolium* extracts having oenothein-B concentrations in excess of 9.6%. In alternative aspects, the present invention provides formulations for treating inflammation or irritation that are prepared from purified oenothein-B obtained from *Epilobium angustifolium*, where the oenothein-B is purified to a concentration of greater than 9.6% prior to formulation. In alternative embodiments, purified oenothein-B from *Epilobium angustifolium* may be utilized in the present invention in concentrations ranging from 9.6% up to concentrations of approximately 100%.

A variety of methods may be used to purify oenotheins from natural sources for use in the various aspects of the present invention. For example, U.S. Pat. No. 5,525,594 (incorporated herein by reference) discloses methods of preparing oenothein-B from plants. Similarly, Ducrey et al., 1996, supra disclose oenothein-A and oenothein-B purification and characterization methods (incorporated herein by reference). Alternative purification methods may be used in accordance with the present invention, provided that they may be used to produce a pharmaceutically acceptable preparation of purified oenothein-B suitable for use in the various aspects of the present invention.

EXAMPLE 1

Figure 3:
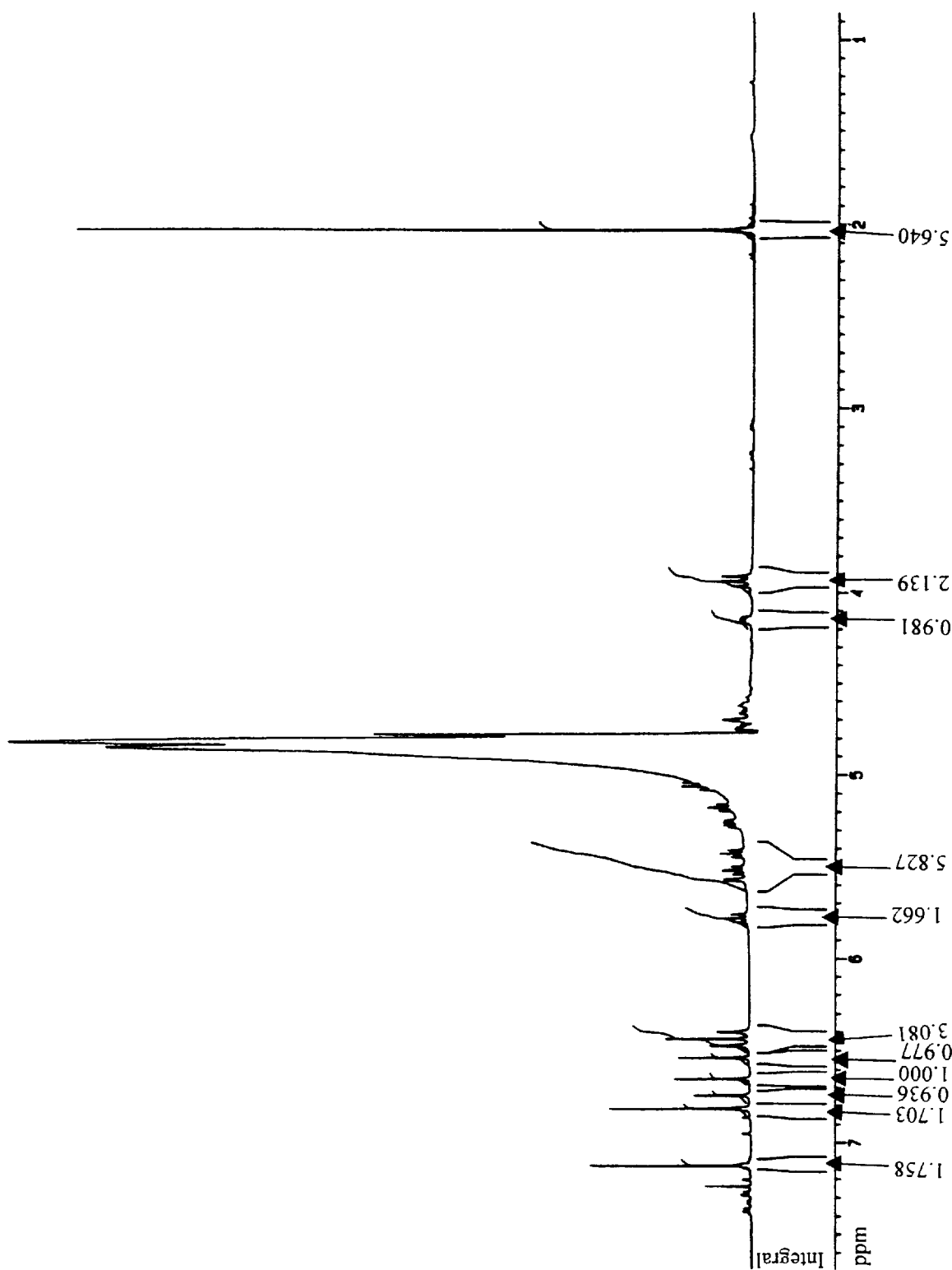
FIG. 3 is 500 MHz 1H NMR spectrum for oenothein-B extracted from New World *E. angustifolium*.
Figure 4:
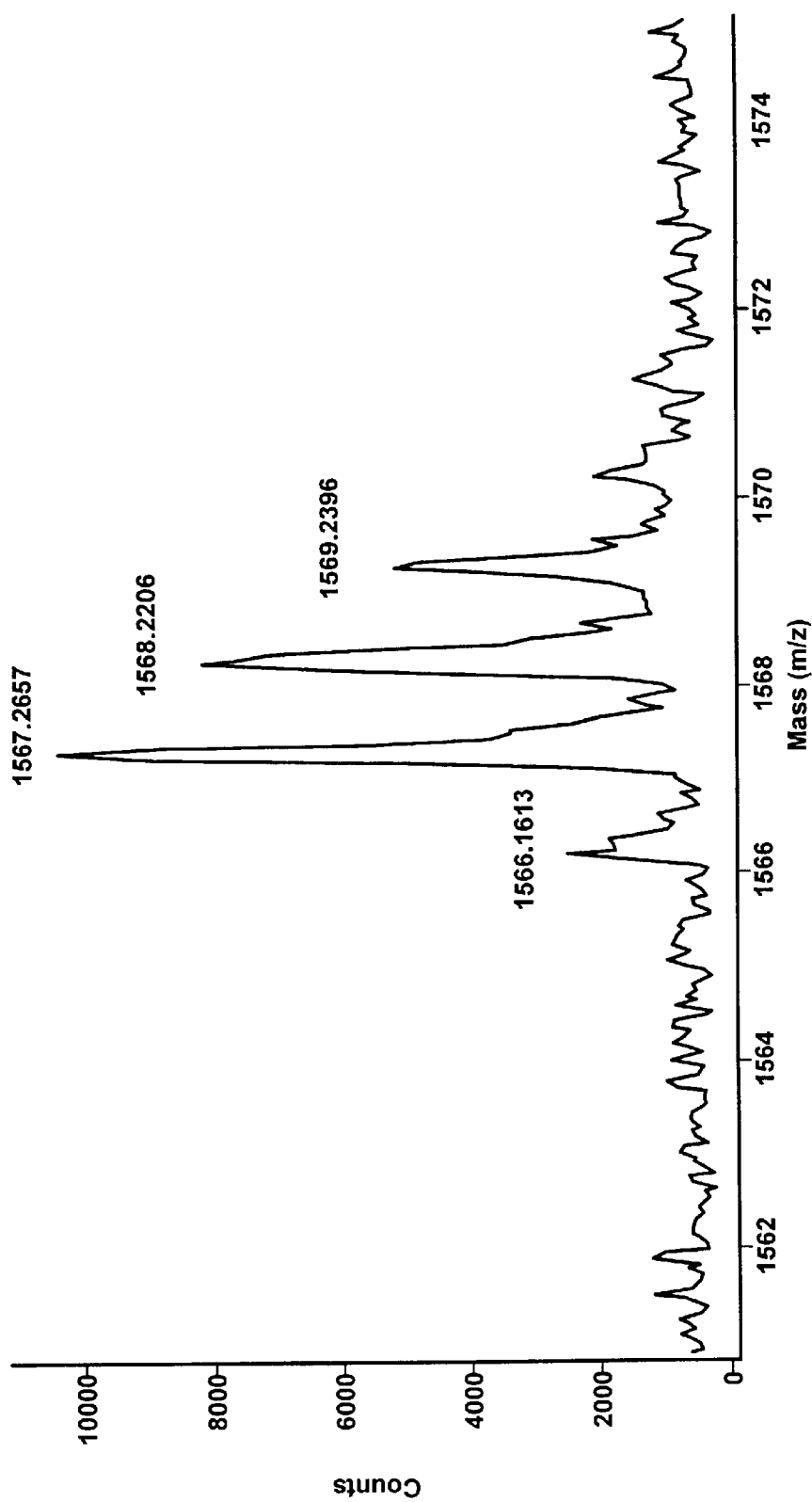
FIG. 4 is a MALDI negative ion mass spectrum for oenothein-B extracted from New World *E. angustifolium*.
Figure 5:
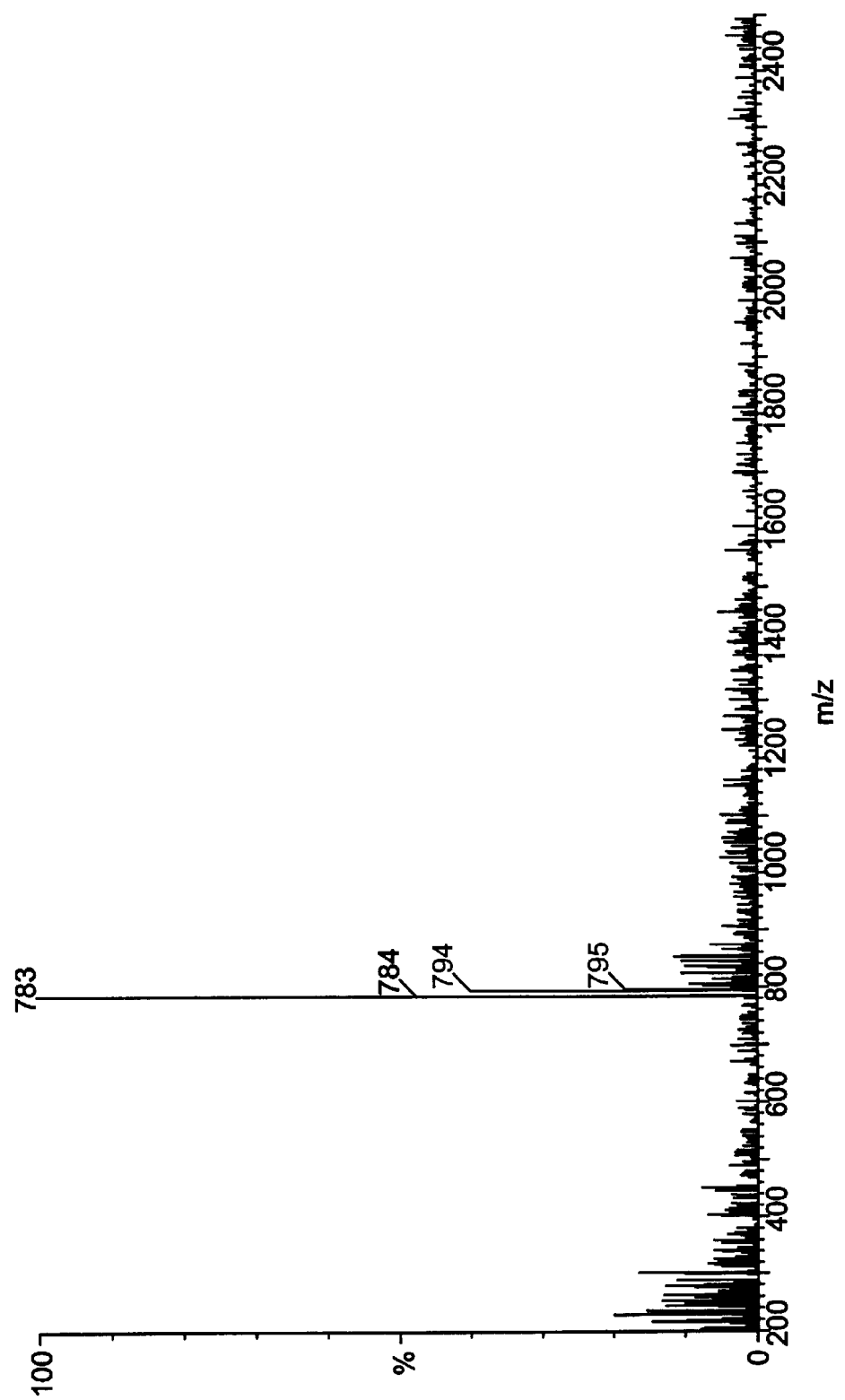
FIG. 5 is a LC-MS APCI (negative ion) mass spectrum for oenothein-B extracted from New World *E. angustifolium*.
Figure 6:
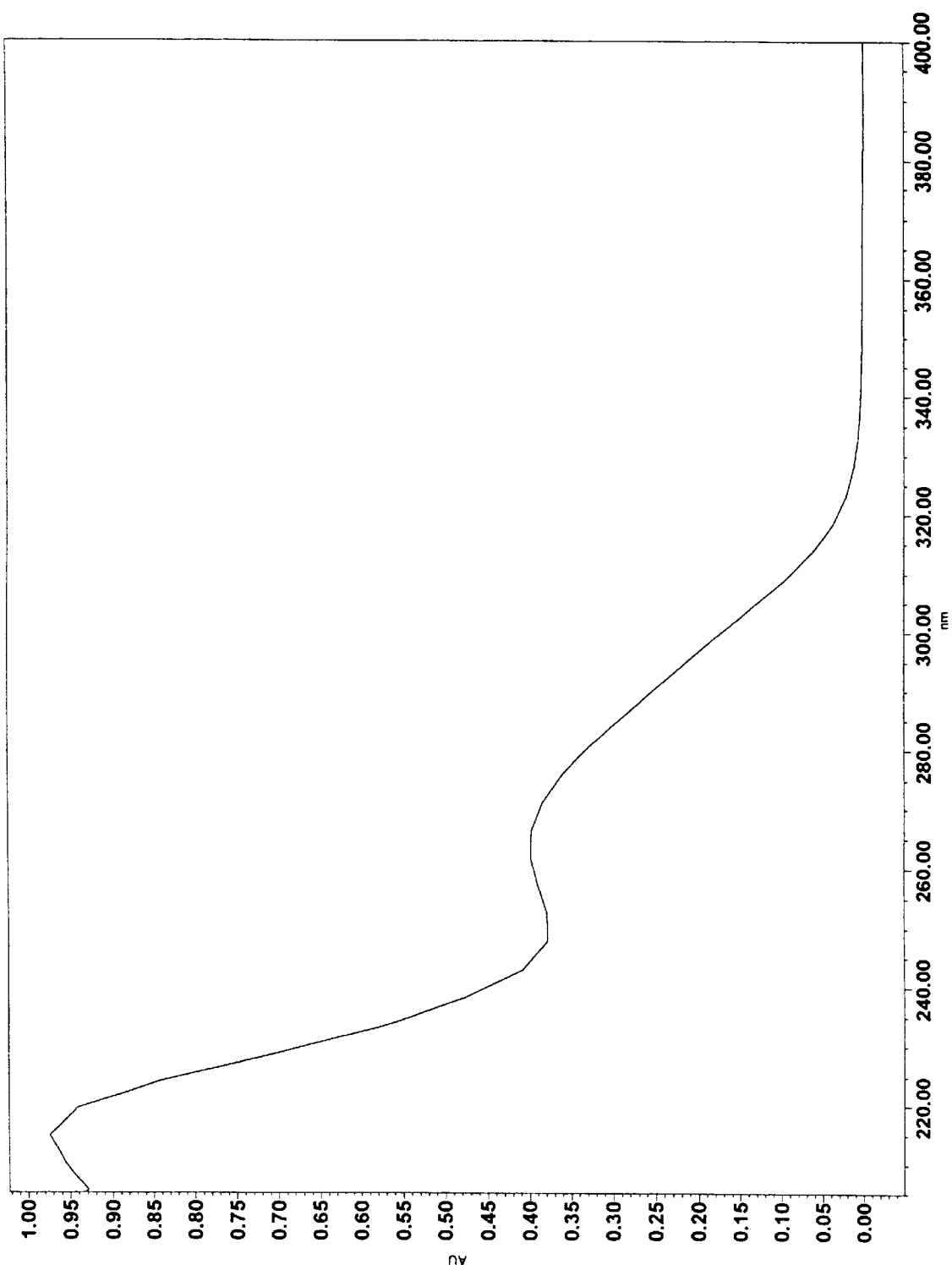
FIG. 6 is a UV-VIS spectrum for oenothein-B extracted from New World *E. angustifolium*.

A purified aqueous extract was obtained from New World *Epilobium angustifolium* (Canadian Willowherb) and subjected to a variety of analytical techniques, which unambiguously identify the purified compound as oenothein-B. This analysis included mass spectroscopy and nuclear magnetic resonance spectrometry, as shown in FIGS. 3 through 6. While oenothein-B was found by these methods to be present in solvent-free aqueous extracts of Canadian Willowherb at levels up to 9.6%, myricetin glucuronide—the substance identified as the active ingredient of the anti-inflammatory action of Old World *Epilobium angustifolium* (see the Background section herein)—was not found in extracts of Canadian Willowherb.

EXAMPLE 2

This example shows the effectiveness of the purified oenothein-B characterized in Example 1 in treating inflammation and irritation.

In the hen's-egg chorioallantoic membrane (CAM) model, in which the CAM is treated with 15% lactic acid as a standard irritant, the development of manifestations of membrane irritation were tracked and scored according to published methods for assessing irritancy (Luepke and Kemper, 1986, *Food and Chemical Toxicology* 24:495; Spielmann et al. 1997, *Food and Chemical Toxicology* 35:39). A sample of the oenothein-B extract from Canadian Willowherb described in Example 1 was tested at a 1% (weight to volume) dilution for activity in the CAM model. The results showed a decrease in irritation by up to 70% when the oenothein-B was applied before the irritant (simulating a prophylactic use) while an 80% decrease was seen with the whole aqueous extract itself.

Further testing was performed with whole aqueous extract of Canadian Willowherb and a whole extract sample spiked with 10% additional oenothein-B. The results showed an increase in the reduction of irritation by the spiked sample of 19% over that of the whole extract by itself.

In human skin patch tests, an oenothein-B extract from Canadian Willowherb formulated in a lotion ameliorated the irritant effects of 15% lactic acid, as measured after 0.5, 1, 4 and 24 hours, compared to controls with no treatment, treatment with water and treatment with the lotion alone (containing no extract).

EXAMPLE 3

This example shows the free radical scavenging activity of oenothein-B. A sample of the oenothein-B extract from Canadian Willowherb described in Example 1 was assessed using the xanthine oxidase/acetaldehyde spectrophotometric method, in which superoxide radical ions are generated in vitro using acetaldehyde and xanthineoxidase, in the presence of test compounds (Fridovich, 1970, *Journal of Biological Chemistry* 245:4053; Hodgson and Fridovich, 1976, *Biochimica et Biophysica Acta* 430:182). The scavenging of free superoxide radicals is quantitated spectrometrically and expressed in terms of percentage of radicals scavenged. Assays were performed with 1% (w/v) and 0.1% (w/v) dilutions of the dried extract, which yielded up to 100% scavenging activity and up to 99% scavenging activity respectively.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to".

What is claimed is:

1. A method of treating a condition in a mammal comprising administering to the mammal a topical formulation of an oenothein, wherein the condition is selected from the group consisting of inflammation, irritation and exposure to free radicals, and wherein the oenothein is selected from the group consisting of:

a) an oenothein extracted or prepared from New World *Epilobium angustifolium* (Canadian Willowherb) and purified to a concentration greater than 9.6% by weight; and b) an oenothein extracted or prepared from a plant source other than New World *Epilobium angustifolium*.

2. The method according to claim 1 wherein the oenothein is oenothein-B or oenothein-A.

3. The method according to claim 1 wherein the oenothein is oenothein-B.

4. The method according to claim 3 wherein the oenothein is applied topically.

5. The method according to claim 4 wherein the mammal is a human.

6. The method according to claim 3 wherein the mammal is a human.

7. The method according to claim 6 wherein the condition is caused by exposure to sunlight.

8. The method according to claim 1 wherein the oenothein is oenothein-A.

9. The method according to claim 8 wherein the oenothein is applied topically.

10. The method according to claim 9 wherein the mammal is a human.

11. The method according to claim 8 wherein the mammal is a human.

12. The method according to claim 11 wherein the condition is caused by exposure to sunlight.

13. The method according to claim 1 wherein the oenothein is applied topically.

14. The method according to claim 13 wherein the mammal is a human.

15. The method according to claim 1 wherein the mammal is a human.

16. The method according to claim 15 wherein the condition is caused by exposure to sunlight.

17. The method according to claim 1 wherein the condition is caused by exposure to sunlight.

18. A method of making a medicament for treating a condition selected from the group consisting of inflammation, irritation and exposure to free radicals, the method comprising formulating the medicament with a known quantity of an oenothein selected from the group consisting of:

a) an oenothein extracted or prepared from New World *Epilobium angustifolium* (Canadian Willowherb) and purified to a concentration greater than 9.6% by weight; and b) an oenothein extracted or prepared from a plant source other than New World *Epilobium angustifolium*.

19. The method according to claim 18 wherein the oenothein is oenothein-B.

20. The method according to claim 18 wherein the oenothein is oenothein-A.

21. A container containing a medicament, wherein the container comprises a label indicating that the medicament is useful for the treatment of a condition selected from the group consisting of inflammation, irritation, exposure to free radicals and exposure to sunlight; and wherein the medicament comprises an oenothein.

22. The container of claim 21 wherein the oenothein is oenothein-A.

23. The container of claim 21 wherein the oenothein is oenothein-B.

24. The container of claim 21 wherein the medicament is formulated for topical application.

* * * * *